(12) United States Patent
Hida et al.

(10) Patent No.: US 9,904,047 B2
(45) Date of Patent: Feb. 27, 2018

(54) IMAGING MECHANISM, ENDOSCOPE, AND METHOD OF MANUFACTURING IMAGING MECHANISM

(71) Applicant: Fujikura Ltd., Koto-ku, Tokyo (JP)

(72) Inventors: Satoshi Hida, Sakura (JP); Takeshi Segi, Sakura (JP); Kenichi Nakatate, Sakura (JP)

(73) Assignee: FUJIKURA LTD., Tokyo (JP)

( * ) Notice: Subject to any disclaimer, the term of this patent is extended or adjusted under 35 U.S.C. 154(b) by 343 days.

(21) Appl. No.: 13/965,956

(22) Filed: Aug. 13, 2013

(65) Prior Publication Data

US 2013/0329026 A1 Dec. 12, 2013

Related U.S. Application Data

(63) Continuation of application No. PCT/JP2013/055594, filed on Feb. 28, 2013.

(30) Foreign Application Priority Data

Mar. 26, 2012 (JP) ................................. 2012-070392

(51) Int. Cl.
*G02B 23/24* (2006.01)
*G02B 7/02* (2006.01)
(Continued)

(52) U.S. Cl.
CPC ...... *G02B 23/2484* (2013.01); *A61B 1/00163* (2013.01); *A61B 1/04* (2013.01);
(Continued)

(58) Field of Classification Search
CPC .... G02B 23/2484; G02B 7/021; G02B 7/025; G02B 23/243; G02B 23/24; G02B 7/02;
(Continued)

(56) References Cited

U.S. PATENT DOCUMENTS 5,657,166 A * 8/1997 Otaki ................. G02B 21/0088
359/661
7,885,010 B1 * 2/2011 Bodor ................. G02B 23/243
359/659

(Continued)

FOREIGN PATENT DOCUMENTS

| CN | 1794944 A | 6/2006 |
| CN | 101526654 A | 9/2009 |

(Continued)

OTHER PUBLICATIONS

International Search Report of PCT/JP2013/055594 dated Apr. 2, 2013.

(Continued)

*Primary Examiner* — Andy Rao
*Assistant Examiner* — Zaihan Jiang
(74) *Attorney, Agent, or Firm* — Sughrue Mion, PLLC

(57) ABSTRACT

An imaging mechanism includes: an imaging device; a light receiving section that is provided on one surface of the imaging device; a cover member that covers the one surface of the imaging device and the light receiving section; and a lens unit that has a plurality of lenses including a plano-convex lens having a flat portion and a lens barrel, and that is optically coupled to the light receiving section, the lens barrel fixing the plurality of lenses, wherein the plano-convex lens having the flat portion is provided at a closest position to the imaging device in the plurality of lenses such that the flat portion faces the imaging device, and the flat portion protrudes from an end of the lens barrel toward the imaging device and is fixed to the cover member.

10 Claims, 6 Drawing Sheets

(51) Int. Cl.
*A61B 1/04* (2006.01)
*A61B 1/00* (2006.01)
*H04N 5/225* (2006.01)

(52) U.S. Cl.
CPC ............. *G02B 7/021* (2013.01); *G02B 7/025* (2013.01); *G02B 23/243* (2013.01); *H04N 2005/2255* (2013.01); *Y10T 29/49002* (2015.01)

(58) Field of Classification Search
CPC . A61B 1/04; A61B 1/00163; Y10T 29/49002; H04N 2005/2255
USPC .................... 348/65; 29/592.1; 359/601, 754
See application file for complete search history.

(56) References Cited

U.S. PATENT DOCUMENTS

| | | | |
|---|---|---|---|
| 2003/0171649 A1 | 9/2003 | Yokoi et al. | |
| 2003/0233024 A1* | 12/2003 | Ando | A61B 1/00096 600/111 |
| 2006/0147197 A1* | 7/2006 | Spruck | G09B 21/008 396/429 |
| 2008/0266441 A1 | 10/2008 | Ichimura | |
| 2009/0225157 A1 | 9/2009 | Orihara et al. | |
| 2009/0296235 A1* | 12/2009 | Igarashi | G02B 23/243 359/720 |

FOREIGN PATENT DOCUMENTS

| | | |
|---|---|---|
| EP | 0978251 A1 | 2/2000 |
| EP | 1455216 A1 | 9/2004 |
| JP | 10-282390 A | 10/1998 |
| JP | 2000-083896 A | 3/2000 |
| JP | 2000-266979 A | 9/2000 |
| JP | 2001-046325 A | 2/2001 |
| JP | 2002-159439 A | 6/2002 |
| JP | 2006-055531 A | 3/2006 |
| JP | 2008-118568 A | 5/2008 |
| JP | 2008-275786 A | 11/2008 |
| WO | 2004086957 A2 | 10/2004 |

OTHER PUBLICATIONS

Machine Translation of JP 2001-046325 A, which was previously filed.
Machine Translation of JP 2008-118568 A, which was previously filed.
Machine Translation of JP 2002-159439 A, which was previously filed.
Machine Translation of JP 10-282390 A, which was previously filed.
Machine Translation of JP 2000-266979 A, which was previously filed.
Machine Translation of JP 2000-083896 A, which was previously filed.
Communication dated Nov. 26, 2013, issued by the Japan Patent Office in corresponding application No. 2012-070392.
Communication dated Aug. 27, 2013, issued by the Japan Patent Office in corresponding application No. 2012-070392.
Communication dated Feb. 10, 2015, issued by the State Intellectual Property Office of the People's Republic of China in corresponding application No. 201380000654.8.
Communication dated Jul. 10, 2015 from the European Patent Office in counterpart application No. 13744939.3.
Communication dated Mar. 10, 2017, from the European Patent Office in counterpart European application No. 13744939.3.

* cited by examiner

IMAGING MECHANISM, ENDOSCOPE, AND METHOD OF MANUFACTURING IMAGING MECHANISM

CROSS REFERENCE TO RELATED APPLICATIONS

This application is a continuation application based on a PCT Patent Application No. PCT/JP2013/055594, filed Feb. 28, 2013, whose priority is claimed on Japanese Patent Application No. No. 2012-070392, filed Mar. 26, 2012, the entire content of which are hereby incorporated by reference.

BACKGROUND OF THE INVENTION

Field of the Invention

The present invention relates to an imaging mechanism mainly added as a component in a fine optical apparatus, such as an endoscope, an endoscope, and a method of manufacturing an imaging mechanism.

Description of the Related Art

In an imaging mechanism mounted in an optical apparatus, such as an endoscope, it is necessary to fix the relative position of a lens and an imaging device so that light emitted from an object to be observed is imaged in a light receiving section (imaging section) of the imaging device.

A method using a light curing adhesive is generally used for fixing the lens. In addition, in order to form an image at the position of the light receiving section, a cap type lens that covers the light receiving section is used in many cases.

In the case of Japanese Unexamined Patent Application, First Publication No. 2008-275786, a lens on the imaging device side has a plurality of legs extending toward the imaging device, and the end surface of the plurality of legs and the front surface of the imaging device are fixed to each other by the light curing adhesive.

In the case of Japanese Unexamined Patent Application, First Publication No. 2006-055531, a first lens group on the rear end side is bonded and fixed to the imaging device with a filter interposed therebetween using an adhesive formed of transparent resin.

In the case of Japanese Unexamined Patent Application, First Publication No. 2008-275786, since a lens frame is provided so as to cover the entire imaging device, the lens frame cannot be made smaller than the imaging device.

In addition, the alignment accuracy in a direction perpendicular to the optical axis of the lens (same horizontal direction as the light receiving surface of the imaging device) depends on the machining accuracy of the end surface of the plurality of legs.

In the case of Japanese Unexamined Patent Application, First Publication No. 2006-055531, since the filter is bonded and fixed to the central portion of the first lens group on the rear end side, the first lens group cannot be made smaller than the filter.

The present invention has been made in view of the above-described situation, and it is an object of the present invention to provide an imaging mechanism, an endoscope, in which the aligning of a lens with respect to a light receiving section of an imaging device is easy and a lens can be miniaturized, and a method of manufacturing the imaging mechanism.

SUMMARY

In order to solve the above-described problem, an imaging mechanism including: an imaging device; a light receiving section that is provided on one surface of the imaging device; a cover member that covers the one surface of the imaging device and the light receiving section; and a lens unit that has a plurality of lenses including a plano-convex lens having a flat portion and a lens barrel, and that is optically coupled to the light receiving section, the lens barrel fixing the plurality of lenses. The plano-convex lens having the flat portion is provided at a closest position to the imaging device in the plurality of lenses such that the flat portion faces the imaging device, and the flat portion protrudes from an end of the lens barrel toward the imaging device and is fixed to the cover member.

It is preferable that the imaging mechanism further include an adhesive that is provided between the plano-convex lens and the cover member and fixes the plano-convex lens to the cover member.

It is preferable that the adhesive be a light curing adhesive.

It is preferable that the imaging mechanism further include a light shielding material that covers a side surface of a portion of the plano-convex lens and an outer surface of the cover member, the portion of the plano-convex lens protruding from the end of the lens barrel.

It is preferable that the lens unit fixe all lenses to one lens barrel, the all lenses being provided closer to an object side than the position of the plano-convex lens.

In addition, an endoscope according to a second aspect of the present invention includes: an imaging mechanism having an imaging device, a light receiving section that is provided on one surface of the imaging device, a cover member that covers the one surface of the imaging device and the light receiving section, and a lens unit that has a plurality of lenses and a lens barrel fixing the plurality of lenses, the plurality of lenses including a plano-convex lens which is provided at a position closest to the imaging device and has a flat portion, the lens unit being optically coupled to the light receiving section; an electrical cable extending toward the imaging mechanism; and a flexible printed circuit board that electrically connects a distal end of the electrical cable to the imaging device. The flat portion protrudes from an end of the lens barrel toward the imaging device and is fixed to the cover member.

In addition, a method of manufacturing an imaging mechanism according to a third aspect of the present invention includes: preparing an imaging device, a light receiving section that is provided on one surface of the imaging device, a cover member that covers the one surface of the imaging device and the light receiving section, and a lens unit that has a plurality of lenses including a plano-convex lens having a flat portion protruding from an end of a lens barrel toward the imaging device, and a lens barrel that fixes the plurality of lenses, the plano-convex lens being provided at a position closest to the imaging device and; and fixing the flat portion to the cover member by aligning the lens unit such that the lens unit is optically coupled to the light receiving section of the imaging device.

It is preferable that the plano-convex lens and the cover member be fixed to each other using an adhesive.

It is preferable that the adhesive be a light curing adhesive.

It is preferable that, when fixing the flat portion of the plano-convex lens to the cover member using the light curing adhesive, the light curing adhesive be cured by emitting light from an object side of the lens unit and also emitting light from a side surface of the plano-convex lens.

It is preferable that the method of manufacturing an imaging mechanism further include: covering a side surface of the plano-convex lens, which protrudes from an end of the lens barrel on the imaging device side, and an outer surface of the cover member by a light shielding material It is preferable that the lens unit fixes all lenses to one lens barrel, the all lenses being provided closer to an object side than the position of the plano-convex lens.

According to the aspects of the present invention described above, in order to fix the flat portion of the plano-convex lens to the cover member, it is possible to align the flat portion of the plano-convex lens and the surface of the cover member while making them shifted from each other sideways. Therefore, high-accuracy optical connection becomes possible without microfabrication.

In addition, according to the aspects of the present invention described above, since the flat portion of the plano-convex lens protrudes from the lens barrel, the object side and the imaging device side can be easily distinguished when fixing the lens unit to the imaging device side.

In addition, according to the aspect of the present invention described above, when using the light curing adhesive, it is possible to cure the adhesive by emitting light from the object side of the lens unit and also emitting light from the side surface of the outer periphery of the plano-convex lens.

In addition, according to the aspect of the present invention described above, the size (cross-sectional area perpendicular to the optical axis of the lens) of the lens unit can be made smaller than the size of the imaging device as necessary.

DESCRIPTION OF THE PREFERRED EMBODIMENTS

Hereinafter, the present invention will be described with reference to the drawings on the basis of a preferred embodiment.

Figure 1A:
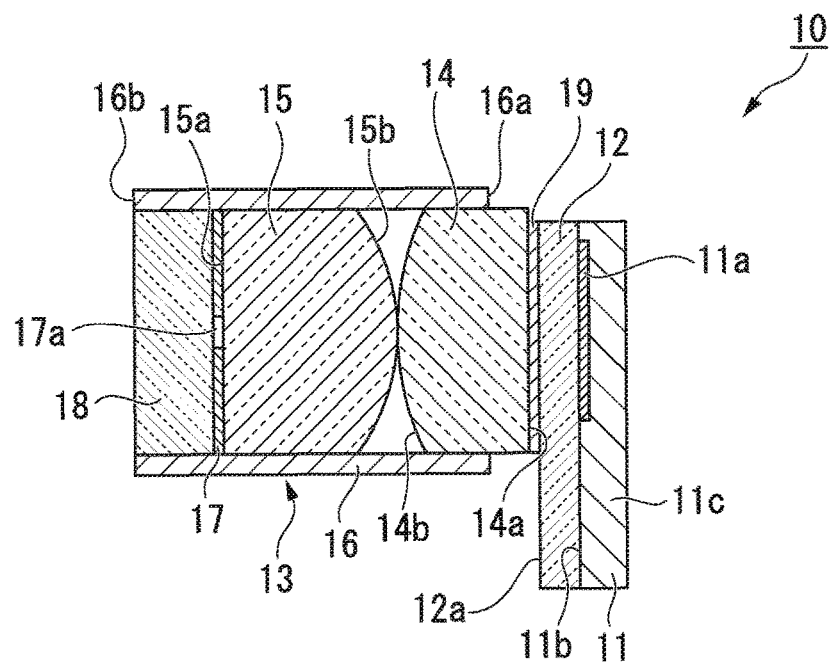
FIG. 1A is a cross-sectional view showing an example of an imaging mechanism according to an embodiment of the present invention.
Figure 1B:
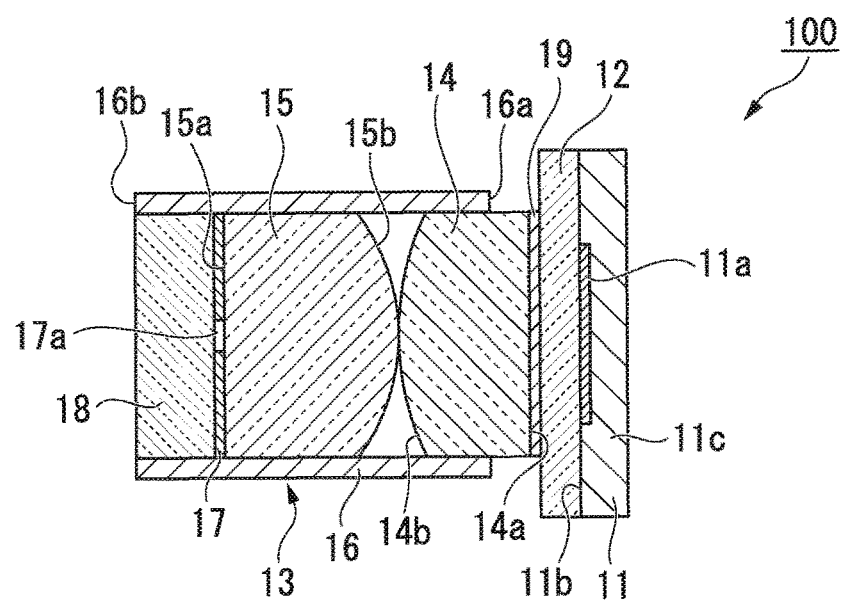
FIG. 1B is a cross-sectional view showing an example of an imaging mechanism according to an embodiment of the present invention.

FIGS. 1A and 1B show examples of an imaging mechanism according to an embodiment of the present invention.

Each of imaging mechanisms 10 and 100 includes an imaging device 11 having a light receiving section 11a provided on one surface 11b, a cover member 12 that covers the surface 11b on which the light receiving section 11a of the imaging device 11 is provided, and a lens unit 13 optically coupled to the light receiving section 11a of the imaging device 11.

Although the imaging device 11 is not particularly limited, semiconductor chips, such as a CMOS (complementary metal oxide semiconductor), a CCD (charge coupled device), and a CPD (charge priming device), can be mentioned.

The chip size is not particularly limited. However, it is preferable to adopt a small chip for the sake of miniaturization.

For example, a chip whose one side (long and short sides) is equal to or less than approximately 1 mm can be mentioned.

It is also possible to use a thin chip having a thickness of tens of micrometers to hundreds of micrometers.

In the light receiving section 11a of the imaging device 11, a microlens for focusing light can also be provided for each pixel.

The cover member 12 covers the light receiving section 11a of the imaging device 11 and the surface 11b on which the light receiving section 11a is provided, and functions as a protective member that protects the light receiving section 11a, an electric circuit (not shown), and the like.

In addition, the thickness of the cover member 12 also functions as a spacer which adjusts the distance (gap) between the light receiving section 11a and the lens unit 13 according to the focal length and optical properties of lenses 14 and 15.

An adhesive (not shown) can also be used to fix the imaging device 11 to the cover member 12.

When the adhesive is located on the light receiving section 11a, it is preferable to use a transparent optical adhesive.

Figure 2A:
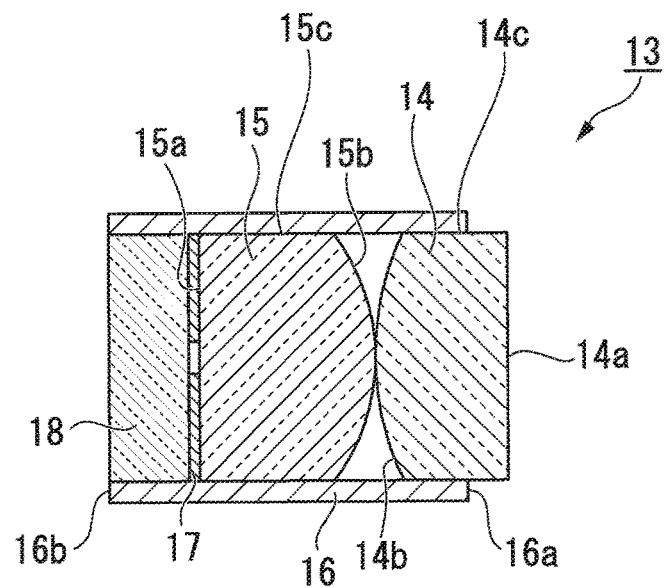
FIG. 2A is a cross-sectional view showing an example of a lens unit.
Figure 2B:
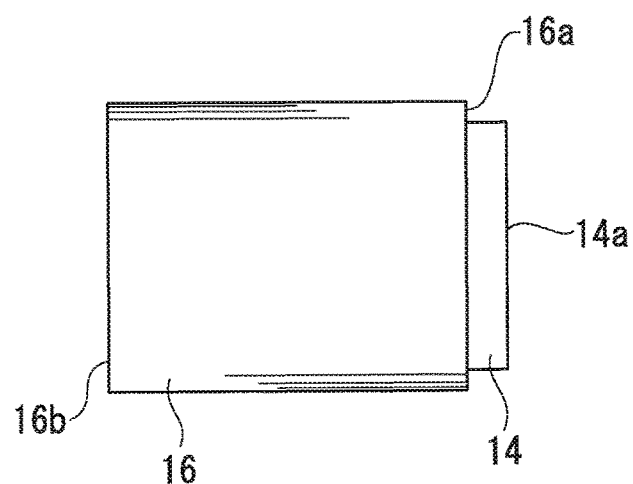
FIG. 2B is a cross-sectional view showing an example of a lens unit.

As shown in FIGS. 2A and 2B, the lens unit 13 includes: a plurality of lenses 14 and 15 including the plano-convex lens 14 on the imaging device 11 side; and a lens barrel 16 that fixes the plurality of lenses 14 and 15.

The lens barrel 16 can be formed of, for example, metal such as SUS, glass, or plastic.

In the lens barrel 16, an imaging device side end 16a and an object side end 16b are open.

Both the lenses 14 and 15 in the illustrated example are plano-convex lenses, and have flat portions 14a and 15a on one side and convex portions 14b and 15b on the other side along the optical axis.

These plano-convex lenses 14 and 15 are fixed by making the convex portions 14b and 15b face each other and performing bonding, engagement, fitting, or the like between side surfaces 14c and 15c and the inner surface of the lens barrel 16.

A transparent cover member 18 is provided on the object side of the lens unit 13.

A diaphragm 17 having an open central portion and a peripheral portion that blocks light is provided between the cover member 18 and the flat portion 15a of the plano-convex lens 15 on the object side.

An opening 17a of the diaphragm 17 is provided at a position through which the optical axis of the lenses 14 and 15 passes.

Optical members, such as the lenses 14 and 15, the cover member 12 of the imaging device 11, and the cover member 18 of the lens unit 13, can be formed of multi-component glass, quartz glass, transparent plastic, single crystal, or the like.

Coating and surface treatment or the like can also be performed on these optical members in order to form an anti-reflection film or the like.

The flat portion 14a of the plano-convex lens 14 on the imaging device side protrudes from the imaging device side end 16a of the lens barrel 16.

Accordingly, when fixing the lens unit 13 to the cover member 12 on the imaging device 11 side using an adhesive or the like, the aligning of the optical axis of the lens unit 13 with respect to the light receiving section 11a can be easily performed by rubbing the flat portion 14a of the plano-convex lens 14 and the surface 12a of the cover member 12, which are planes, against each other without interference of the end 16a of the lens barrel 16. Accordingly, the aligning of the optical axis of the lens unit 13 with respect to the light receiving section 11a can be easily performed.

Although the shape and size of each portion of the lens unit 13 are not particularly limited, the convex portion 15b of the lens 15 on the object side is a spherical surface having a radius of 1 mm and the convex portion 14b of the lens 14 on the imaging device side is a spherical surface having a radius of 2 mm in an embodiment.

The internal diameter of the lens barrel 16 is 0.6 mm, the length of the lens barrel 16 is 0.8 mm, the wall thickness of the lens barrel 16 is 0.03 mm, and the length of the flat portion 14a of the imaging device side plano-convex lens 14 from the lens barrel end 16a to the protruding portion is 0.1 mm.

Each component of the imaging mechanisms 10 and 100 shown in FIGS. 1A and 1B can be manufactured by using a manufacturing method including the following steps (1) to (3).

The order of steps (1) and (2) is arbitrary, and the steps (1) and (2) can also be performed simultaneously.

(1) Step of covering the light receiving section 11a of the imaging device 11 and the surface 11b, on which the light receiving section 11a is provided, with the cover member 12.

(2) Step of manufacturing the lens unit 13 by fixing a plurality of lenses 14 and 15 such that the flat portion 14a of the plano-convex lens 14 on the imaging device 11 side protrudes from the end 16a of the lens barrel 16 on the imaging device 11 side.

(3) Step of aligning the flat portion 14a of the plano-convex lens 14, which protrudes from the end 16a of the lens barrel 16 on the imaging device 11 side, so as to optically couple the lens unit 13 with the light receiving section 11a of the imaging device 11, and fixing the flat portion 14a of the plano-convex lens 14 to the cover member 12, which covers the light receiving section 11a and the surface 11b.

Before the step of fixing the flat portion 14a of the plano-convex lens 14 to the cover member 12, the imaging device 11, in which the light receiving section 11a and the surface 11b on which the light receiving section 11a is provided are covered by the cover member 12, and the lens unit 13, in which a plurality of lenses 14 and 15 are fixed to the lens barrel 16, are prepared.

Accordingly, the position of the imaging device 11 and the lens unit 13 can be aligned while actually observing light (image) received by the imaging device 11 through the lens unit 13.

When fixing the plano-convex lens 14 and the cover member 12 to each other using an adhesive 19, the optical axis of the lens unit 13 and the optical axis of the light receiving section 11a are aligned by displacing the plano-convex lens 14 (lens unit 13) or the cover member 12 (imaging device 11) while the adhesive 19 is not cured and has fluidity.

As the adhesive 19, a thermosetting adhesive, a chemical reactive adhesive, and the like can be mentioned. However, since a light curing adhesive can be cured quickly and an uncured state can be made to continue when necessary, the light curing adhesive is preferable.

As the irradiation light, ultraviolet light and visible light can be mentioned.

As the optical adhesive, silicone, epoxy, fluorinated epoxy, acrylic, epoxy acrylate, fluorinated epoxy acrylate, and the like can be mentioned.

In addition, according to the lens unit 13 in the illustrated example, the lens unit 13 can be combined without changing the specifications of the lens unit 13 even if the light receiving section 11a is disposed at a position biased to the outer peripheral portion of the surface 11b of the imaging device 11 as shown in FIG. 1A or even if the light receiving section 11a is disposed in a central portion of the surface 11b of the imaging device 11 as shown in FIG. 1B.

In this manner, the degree of freedom when designing the position of the light receiving section 11a in the imaging device 11 together with the positions of other circuits, terminals, or the like is improved.

As shown in FIG. 1A, a part of the flat portion 14a of the plano-convex lens 14 can also be fixed in a state where it protrudes outward from the surface 12a of the cover member 12.

Figure 3A:
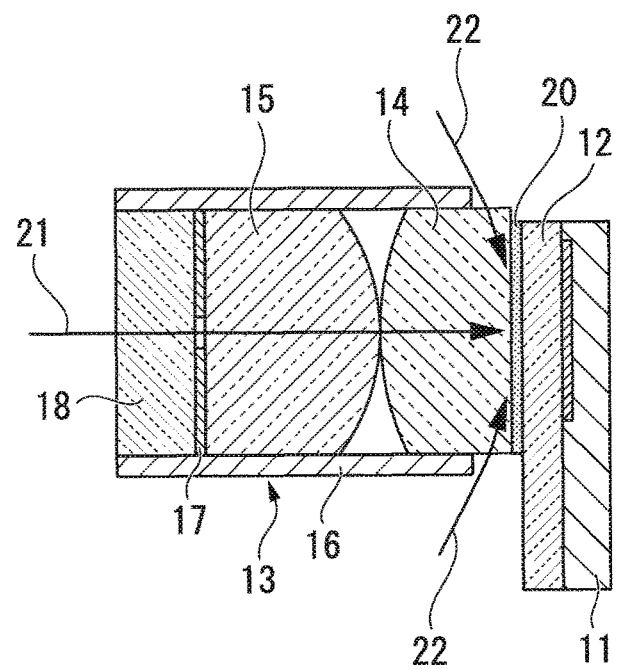
FIG. 3A is a cross-sectional view showing an example of a method of photo-curing an adhesive.
Figure 3B:
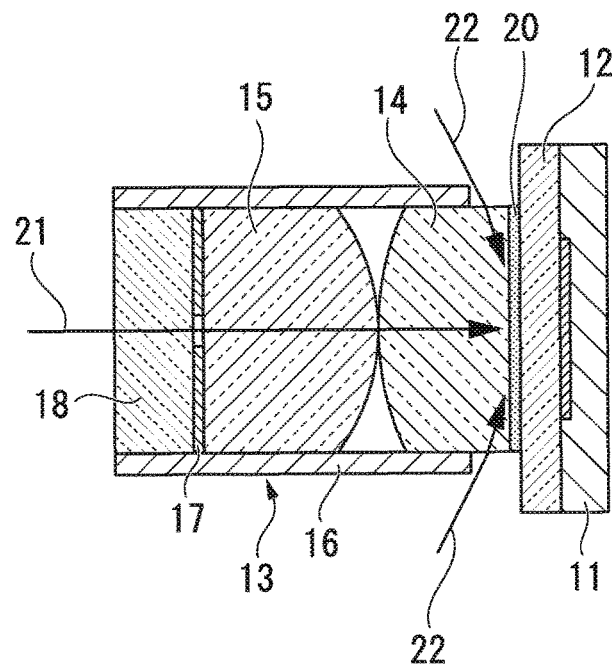
FIG. 3B is a cross-sectional view showing an example of a method of photo-curing an adhesive.

When fixing the flat portion 14a of the plano-convex lens 14 to the cover member using a light curing adhesive, it is preferable to cure a light curing adhesive 20 by emitting light 21 from the object side of the lens unit 13 and also emitting light 22 from the side surface of the outer periphery of the plano-convex lens 14 protruding from the end 16a of the lens barrel 16 as shown in FIGS. 3A and 3B.

In addition, FIGS. 3A and 3B show a state where the adhesive 20 are not completely cured.

Since the main irradiation light 21 emitted from the object side of the lens unit 13 is emitted to a region including a portion, through which image light passes at the time of actual observation, it is possible to cure most of the adhesive 20.

In addition, the auxiliary irradiation light 22 emitted from the outer periphery of the plano-convex lens 14 can reliably cure the adhesive 20 of the periphery.

In particular, when aligning the lens unit 13 with respect to the light receiving section 11a, even if the amount of the adhesive 20 running off the plano-convex lens 14 is increased, it is possible to suppress a situation where the adhesive 20 remains uncured.

Since the plano-convex lens 14 and the cover member 12 allow light to be transmitted therethrough, it is necessary to suppress the influence of emission light (light leakage) emitted laterally or incident light (noise) incident from the side.

Therefore, as shown in FIGS. 4A to 5B, it is preferable to cover the side surface of the outer periphery of the plano-convex lens 14, which protrudes from the lens barrel 16, and the outer surface of the cover member 12 with a light shielding material 23.

As the light shielding material 23, a resin, adhesive, and the like in which a colorant, an absorption material, or the like is mixed can be used.

It is preferable to use a thermosetting resin, in which a black material (powder) such as carbon is dispersed, as the light shielding material 23 since the thermosetting resin is excellent in light shielding and heat resistance.

Figure 4A:
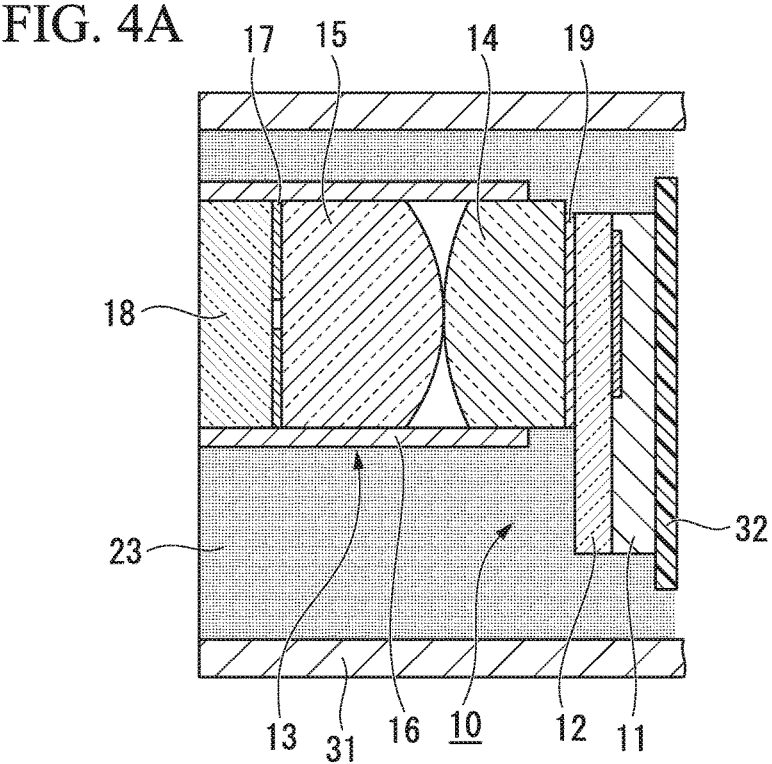
FIG. 4A is a partial sectional view showing an example of the endoscope end structure.
Figure 4B:
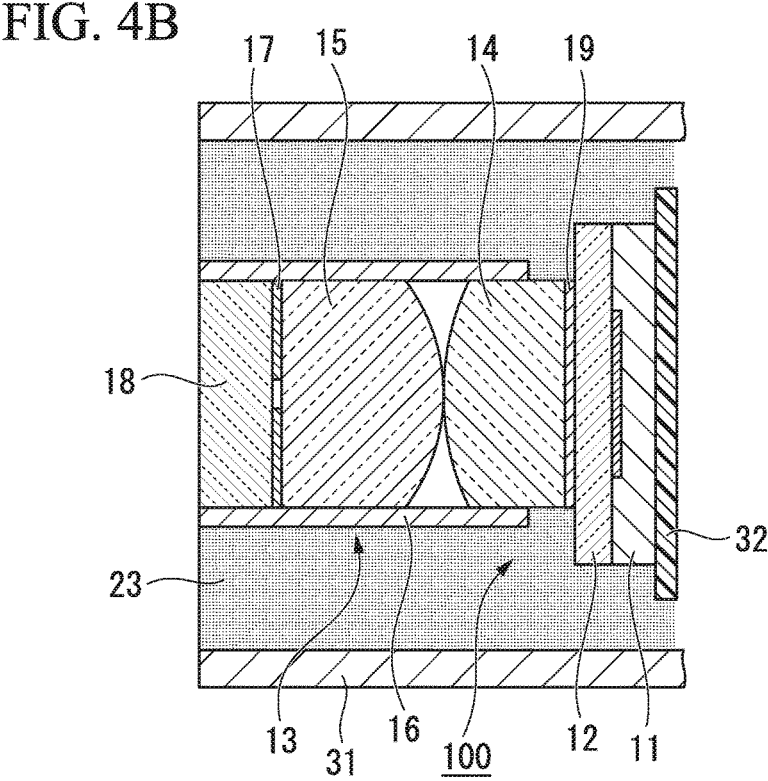
FIG. 4B is a partial sectional view showing an example of the endoscope end structure.

FIGS. 4A and 4B show examples in which the inside of an outer cylinder 31, which covers each of the imaging mechanisms 10 and 100, is filled with the light shielding material 23.

In this case, it is preferable to fill the light shielding material 23 after housing each of the imaging mechanisms 10 and 100 in the outer cylinder 31 and solidify it.

Figure 5A:
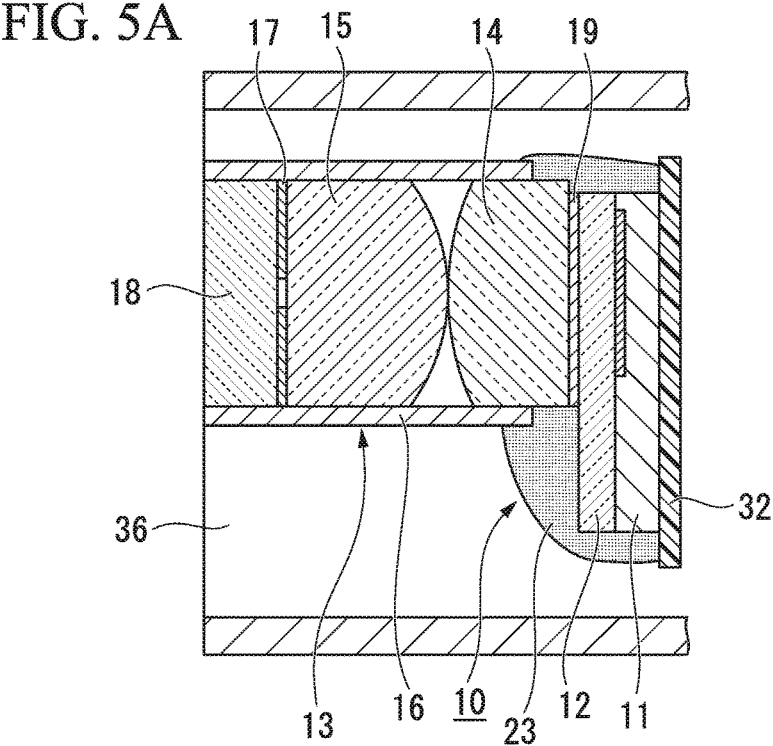
FIG. 5A is a partial sectional view showing an example of the endoscope end structure.
Figure 5B:
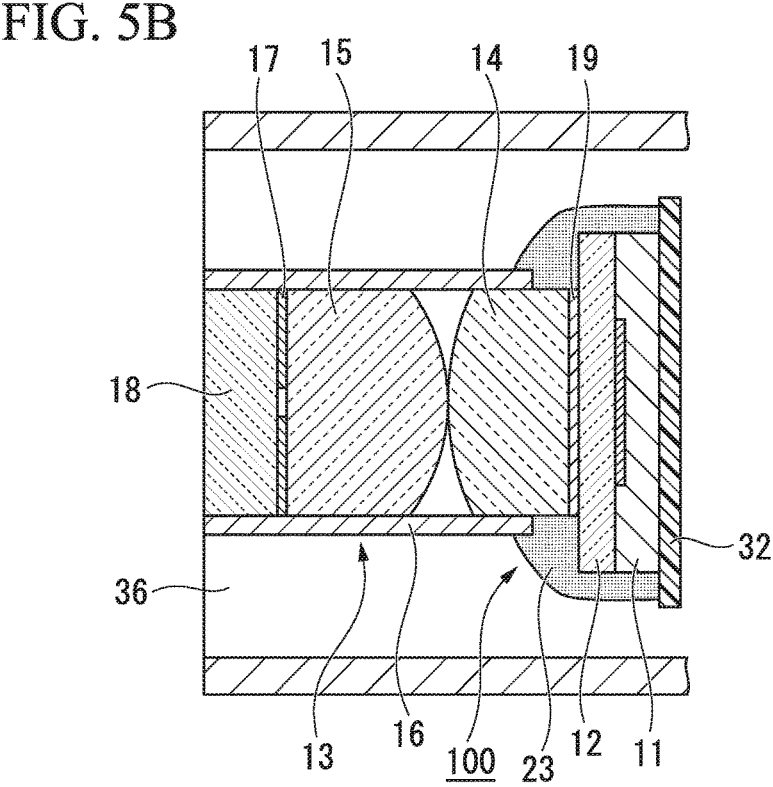
FIG. 5B is a partial sectional view showing an example of the endoscope end structure.

In addition, FIGS. 5A and 5B show examples in which the light shielding material 23 is bonded only to the side surface of the outer periphery of the plano-convex lens 14 protruding from the lens barrel 16, the outer surface of the cover member 12, and nearby regions.

In this case, it is also possible to bond the light shielding material 23 to each of the imaging mechanisms 10 and 100 and then house them in the outer cylinder 31.

In addition, a space 36 between the outer cylinder 31 and each of the imaging mechanisms 10 and 100 may be a cavity, or the space 36 may be filled with a filling material or sealant, such as resin, so that the outer cylinder 31 is sealed. This sealant or filling material may block light or may allow light to be transmitted therethrough.

The space 36 may also be filled using a resin or adhesive having a fluidity of viscosity of approximately thousands of CPS, and then the resin or adhesive may be solidified or cured.

When a hard resin is used as the light shielding material 23, sealant, or filling material, heat shrinkage is unlikely to occur. Accordingly, this is suitable for applications for repeatedly performing sterilization or heat treatment.

In this case, as the hardness of the resin, D80 or so can be mentioned at Shore D (for example, type D Durometer of JIS K6253).

When a soft resin is used as the light shielding material 23, sealant, or filling material, there is an advantage in that it is easy to absorb the stress and the impact resistance is excellent.

In this case, as the hardness of the resin, A30 or so can be mentioned at Shore A (for example, type A Durometer of JIS K6253).

Figure 6:
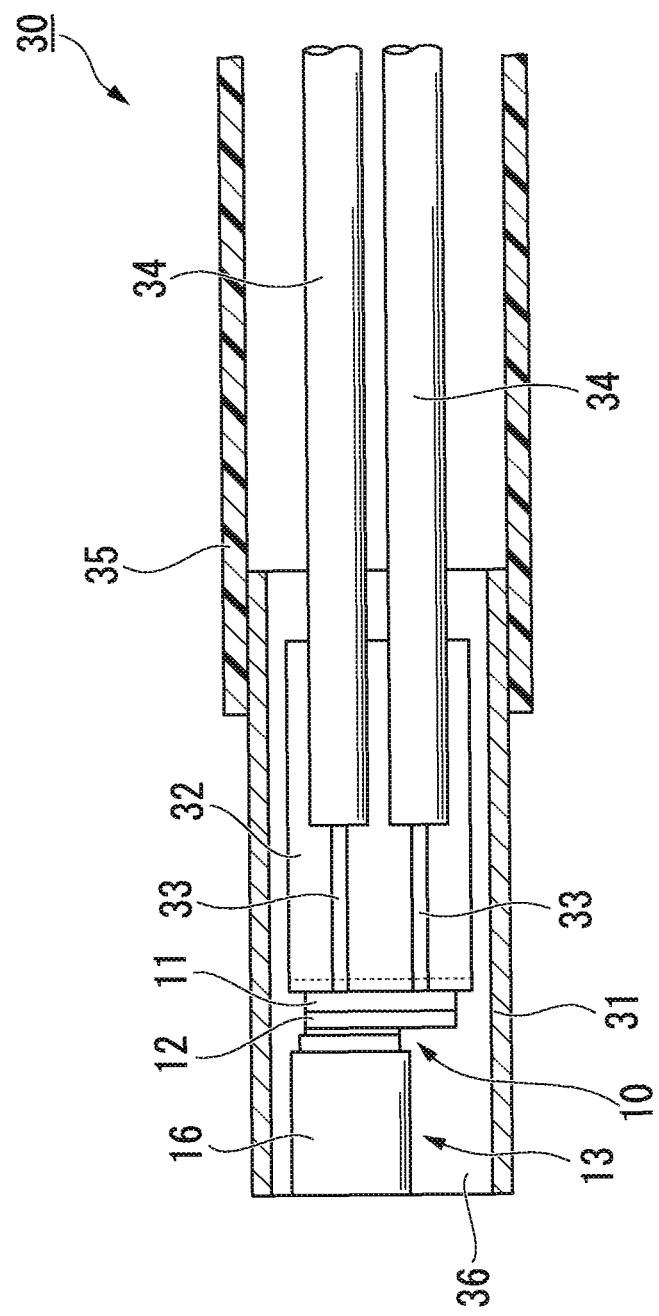
FIG. 6 is a partial sectional view showing an example of an endoscope.

FIG. 6 shows an example of an endoscope including the imaging mechanism 10 of the present embodiment.

This endoscope 30 includes an electrical cable 34 extending toward the imaging mechanism 10 and a flexible printed circuit board 32 that electrically connects the distal end of the electrical cable 34 to the imaging device 11.

As a method of fixing the imaging device 11 to the flexible printed circuit board 32, a bonding material, such as an adhesive, solder, or silver solder, or mechanical means, such as a screw, may be provided on the back surface 11c or the side surface of the imaging device 11.

The imaging device 11 is housed in the sleeve-shaped outer cylinder 31.

The size of the outer cylinder 31 is not particularly limited. For example, the external diameter of the outer cylinder 31 may be approximately 1.2 mm, and the length of the outer cylinder 31 may be approximately 5 mm.

The outer cylinder 31 can be formed of, for example, metal resin, such as SUS, or glass.

As the flexible printed circuit board 32, a wiring board in which metal layers including copper foil are formed on one or both sides of a flexible insulating film can be used.

As the insulating film, polyimide, polyester, liquid crystal polymer, and the like can be used. However, the insulating film is not particularly limited to these.

The flexible printed circuit board 32 has a wiring line 33 formed of a pattern-like conductor, and electrically connects the electrical cable 34 and the imaging device 11 to each other.

Conductive members, such as solder bumps, metal wires, an anisotropic conducting material, or conductive paste, can be used for the electrical connection between the wiring line 33 and the imaging device 11.

A coat formed of an electrically insulating material can be provided in electrical connection means, such as a wiring line.

The electrical cable 34 in the illustrated example is housed in a tube 35.

It is preferable that the tube 35 be flexible.

In the lens unit 13, it is preferable to fix all the lenses 14 and 15, which are provided closer to the object side than the plano-convex lens 14 is, to one lens barrel 16.

Thus, the lens barrel 16 is fixedly positioned relative to the imaging device 11 through the plano-convex lens 14 and the cover member 12. This is advantageous in miniaturization and cost reduction since the number of members can be reduced.

While the present invention has been described on the basis of the preferred embodiment, the present invention is not limited to the above-described embodiment, various modifications can be made without departing from the concept of the present invention.

The imaging mechanism 10 of the present embodiment can be used in a state of being inserted in a catheter or can be built in various electronic apparatuses, without being limited to the case where it is built in the endoscope.

In the case of an endoscope used in a body cavity, the imaging mechanism 10 needs to be sterilized at least once. In the case of an endoscope that is repeatedly used, sterilization is performed each time (before use and after use).

As a sterilization method, for example, ethylene oxide gas treatment or low-temperature plasma treatment of 60° C. can be used.

An endoscope can also include a light guide for illumination.

In addition, it is also possible to have a path for inserting a tube for supplying a nutritional supplement, drug solution, or the like.

What is claimed is:

1. An imaging mechanism housed in an outer cylinder, the imaging mechanism comprising:
   an imaging device which is a semiconductor chip in a plate shape;
   a light receiving section that is provided on one surface of the imaging device;
   a cover member that covers the one surface of the imaging device and the light receiving section;
   a lens unit that has a plurality of lenses including a plano-convex lens having a flat portion and a lens barrel, and that is optically coupled to the light receiving section, the lens barrel fixing the plurality of lenses; and
   a light shielding material that directly covers a side surface of a portion of the plano-convex lens and an outer surface of the cover member, the portion of the plano-convex lens protruding from the end of the lens barrel, wherein
   the outer cylinder and the imaging mechanism form a space therebetween, and the space is a cavity or is filled with a filling material or sealant,
   the plano-convex lens having the flat portion is provided at a closest position to the imaging device in the plurality of lenses such that the flat portion faces the one surface of the imaging device, the flat portion protrudes from an end of the lens barrel toward the one surface of the imaging device and is fixed to the cover member, and the light receiving section is arranged between the imaging device and the cover member.

2. The imaging mechanism according to claim 1, further comprising:

an adhesive that is provided between the plano-convex lens and the cover member and fixes the plano-convex lens to the cover member.

3. The imaging mechanism according to claim 2, wherein the adhesive is a light curing adhesive.

4. The imaging mechanism according to claim 1, wherein the lens unit fixes all lenses to one lens barrel, the all lenses being provided closer to an object side than the position of the plano-convex lens.

5. An endoscope comprising:

an outer cylinder;

an imaging mechanism which is housed in the outer cylinder, the imaging mechanism having: an imaging device which is a semiconductor chip in a plate shape; a light receiving section that is provided on one surface of the imaging device; a cover member that covers the one surface of the imaging device and the light receiving section; a lens unit that has a plurality of lenses and a lens barrel fixing the plurality of lenses; and a light shielding material that directly covers a side surface of a portion of the plano-convex lens protruding from the end of the lens barrel and an outer surface of the cover member, the outer cylinder and the imaging mechanism which form a space therebetween, the space being a cavity or being filled with a filling material or sealant, the plurality of lenses including a plano-convex lens which is provided at a position closest to the imaging device and has a flat portion, the lens unit being optically coupled to the light receiving section, and the flat portion facing the one surface of the imaging device;

an electrical cable extending toward the imaging mechanism; and a flexible printed circuit board that electrically connects a distal end of the electrical cable to the imaging device, wherein the flat portion protrudes from an end of the lens barrel toward the one surface of the imaging device and is fixed to the cover member, and the light receiving section is arranged between the imaging device and the cover member.

6. A method of manufacturing an imaging mechanism housed in an outer cylinder, the method comprising:

preparing an imaging device which is a semiconductor chip in a plate shape; a light receiving section that is provided on one surface of the imaging device; a cover member that covers the one surface of the imaging device and the light receiving section so that the light receiving section is arranged between the imaging device and the cover member; a lens unit that has a plurality of lenses including a plano-convex lens having a flat portion protruding from an end of a lens barrel toward the imaging device, and a lens barrel that fixes the plurality of lenses, the plano-convex lens being provided at a position closest to the imaging device, the flat portion facing the one surface of the imaging device; a light shielding material that directly covers a side surface of a portion of the plano-convex lens protruding from the end of the lens barrel and an outer surface of the cover member, the outer cylinder and the imaging mechanism which form a space therebetween, and the space being a cavity or being filled with a filling material or sealant; and fixing the flat portion to the cover member by aligning the lens unit such that the lens unit is optically coupled to the light receiving section of the imaging device.

7. The method of manufacturing an imaging mechanism according to claim 6, wherein the plano-convex lens and the cover member are fixed to each other using an adhesive.

8. The method of manufacturing an imaging mechanism according to claim 7, wherein the adhesive is a light curing adhesive.

9. The method of manufacturing an imaging mechanism according to claim 8, wherein when fixing the flat portion of the plano-convex lens to the cover member using the light curing adhesive, the light curing adhesive is cured by emitting light from an object side of the lens unit and emitting light from a side surface of the plano-convex lens.

10. The method of manufacturing an imaging mechanism according to claim 6, wherein the lens unit fixes all lenses to one lens barrel, the all lenses being provided closer to an object side than the position of the plano-convex lens.

* * * * *